United States Patent
Grimaldi et al.

(10) Patent No.: US 6,992,225 B2
(45) Date of Patent: *Jan. 31, 2006

(54) ORGANIC PEROXIDE HEAT STABILIZER

(75) Inventors: Sandra Grimaldi, Sainte Foy-les-Lyon (FR); Olivier Guerret, Mazerol (FR); Jean-Luc Couturier, Lyons (FR); Fabien Debaud, Lyons (FR)

(73) Assignee: Arkema, Puteaux (FR)

( * ) Notice: Subject to any disclaimer, the term of this patent is extended or adjusted under 35 U.S.C. 154(b) by 128 days.

This patent is subject to a terminal disclaimer.

(21) Appl. No.: 10/478,035

(22) PCT Filed: Apr. 30, 2002

(86) PCT No.: PCT/FR02/01500

§ 371 (c)(1),
(2), (4) Date: Nov. 17, 2003

(87) PCT Pub. No.: WO02/092561

PCT Pub. Date: Nov. 21, 2002

(65) Prior Publication Data

US 2004/0138081 A1    Jul. 15, 2004

(30) Foreign Application Priority Data

May 17, 2001   (FR) .................................. 02 96526

(51) Int. Cl.
    C07C 409/00    (2006.01)
    C07C 409/02    (2006.01)
    C07C 409/16    (2006.01)
    C07C 409/24    (2006.01)
(52) U.S. Cl. .......................... 568/559; 562/3; 558/261; 560/2; 560/3; 560/4
(58) Field of Classification Search ............... 558/261; 560/2, 3, 4; 562/3; 568/559
See application file for complete search history.

(56) References Cited

U.S. PATENT DOCUMENTS

| 3,702,869 | A |   | 11/1972 | Leveskis et al. |
| 4,129,517 | A | * | 12/1978 | Eggensperger et al. 252/186.23 |
| 5,098,607 | A |   | 3/1992  | Inaba et al. |
| 5,739,096 | A |   | 4/1998  | Rees |
| 6,620,892 | B1| * | 9/2003  | Bertin et al. ................ 525/259 |

FOREIGN PATENT DOCUMENTS

| AU | 8942933 A | * | 4/1990 |
| FR | 1.594.180 |   | 7/1970 |
| FR | 2792321 A1| * | 10/2000 |
| NL | 7401405   |   | 4/1974 |
| WO | WO 00/63260 |  | 10/2000 |
| WO | WO 03/060052 A1 | * | 7/2003 |

OTHER PUBLICATIONS

USPTO obtained translation of NL 7401405.*
WPI Acc No: 2000-298623/~200026~; JP2000/086816-A (Sep. 11, 1998).
WPI Acc No: 1990-246880/199033; AU 8942933 (Oct. 16, 1989).

* cited by examiner

Primary Examiner—Matthew A. Thexton
(74) Attorney, Agent, or Firm—Steven D. Boyd

(57) ABSTRACT

The invention concerns a heat stabilizer of organic peroxides characterized in that it is an N-hetrocyclic compound which contains at least one nitroxyl radical with the N atom of the nitroxyl radical forming part of the ring. The invention also concerns a storage-stable and heat-stable organic peroxide composition containing an N-hetrocyclic compound which contains at least one nitroxyl radical with the N atom of the nitroxyl radical forming part of the ring, the method for preparing the same and uses thereof for modifying polymers.

11 Claims, No Drawings

ORGANIC PEROXIDE HEAT STABILIZER

FIELD OF THE INVENTION

The present invention relates to a heat stabilizer for organic peroxides. Another subject-matter of the invention is a composition comprising organic peroxides which is stable on storage and stable toward heat.

BACKGROUND OF THE INVENTION

The use of a solvent, miscible with a (lower) alkyl ketone peroxide and exhibiting a boiling point of between approximately 185 and 225° C., for thermally stabilizing organic peroxide has been disclosed in the document FR 1 594 180. This document teaches that the solvent is chosen from esters, aldehydes, ketones, hydrocarbons, halogenated hydrocarbons and epoxides. It also teaches that, in addition to the heat-desensitizing solvent, pyrrolidine stabilizers can be used to render the ketone peroxides stable on storage.

French Application FR 2 792 321 discloses a process for the manufacture of a controlled-rheology resin from a homopropylene or propylene copolymer in which, in place of the peroxides of the state of the art or in addition to the latter, stable free radicals, such as nitroxides, are incorporated in the resin to be modified, introduced, for example, into the molten zone of an extruder.

Nitroxyl radicals are highly stable radical entities having an N—O functional group. Reference may be made to the publication by D. Griller and K. Ingold in Accounts of Chemical Research, 1976, 9, 13–19, or to that by A. Forrester et al. "Organic Chemistry of Stable Free Radicals" in Academic Press, 1968, for the definition.

These radicals have the property of reacting very rapidly with carbonaceous radicals resulting from the decomposition of initiators or resulting from radical processes, such as radical polymerizations. This reactivity has been taken advantage of by incorporating these nitroxyl radicals in radical polymerization processes, such as the polymerization of styrene or acrylates, or processes for the copolymerization, decomposition or modification of polypropylene.

The Applicant Company has just found that nitroxyl radicals can thermally stabilize peroxides and make it possible optionally to increase the stability of the latter on storage.

DESCRIPTION OF THE INVENTION

A first subject-matter of the present invention is a heat stabilizer for organic peroxides, characterized in that it includes at least one nitroxyl radical in its molecule. Preferably, the heat stabilizer for organic peroxides is an N-heterocyclic compound with the nitrogen atom of the nitroxyl radical forming part of the ring.

Mention may in particular be made, as heat stabilizer, of the compounds represented by the formulae (I), (II) and (III):

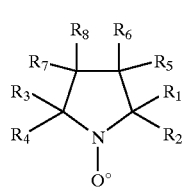
(I)

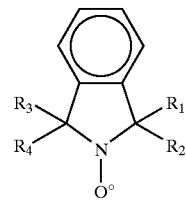
(II)

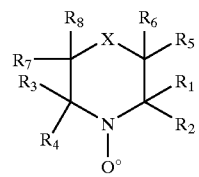
(III)

in which $R_1$, $R_2$, $R_3$ and $R_4$, which can be identical or different, represent a hydrogen atom, a halogen atom, such as fluorine, chlorine, bromine or iodine, a saturated or unsaturated and linear, branched or cyclic hydrocarbonaceous group, such as an alkyl or phenyl radical, a polymer chain, which can, for example, be a chain of poly(alkyl (meth)acrylate), such as poly(methyl methacrylate), of polydiene, of polyolefin or of polystyrene, or a functional group, such as a cyano group —CN, an ester group —COOR, an amide group —CON(R)$_2$, an alkoxyl group —OR or a phosphonate group —PO(OR)$_2$ in which R represents a hydrocarbonaceous chain having from 1 to 9 carbon atoms, and in which $R_5$, $R_6$, $R_7$ and $R_8$, which can be identical or different, can be chosen from the same family of group as that which has just been envisaged for $R_1$, $R_2$, $R_3$ and $R_4$ and, furthermore, can represent a hydroxyl group —OH or an acid group, such as —COOH or —PO(OH)$_2$ or —SO$_3$H. Furthermore, X in the formula (III) represents a divalent group chosen from methylene —CH$_2$—, —C(OR°)(OR')—, carbonyl —C(O)—, oxy —O— and —CHZ-, with Z representing a monovalent residue chosen from cyano: —CN, hydroxyl: —OH, amino: —NR°R', alkoxy: —OR°, iminoyl: —N=CR°R', carboxylate: —OC(O)—R° or amide: —NHR°—C(O)R' groups, in which R° and R', which are identical or different, represent a hydrogen atom, a linear or branched alkyl group having a number of carbon atoms ranging from 1 to 20, or a benzyl or phenyl group. In the formula (III), X can also represent a phosphonate group: —OP(O)R"R'"— with R" and R'" having the same meaning as Z.

The compounds represented by the general formula (IV)

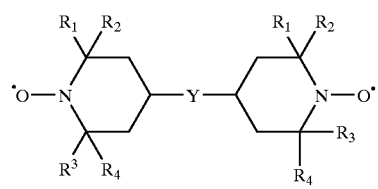
(IV)

in which $R_1$, $R_2$, $R_3$ and $R_4$, which can be identical or different, have the same meaning as those used for the formulae (I) to (III) and Y represents a divalent group chosen from:
—OC(O)—(CR$_a$R$_b$)$_n$—C(O)O—,
—NH—(CR$_a$R$_b$)$_n$NH—, —NHC(O)—(CR$_a$R$_b$)$_n$—C(O)NH—, —S—, —O—; R$_a$ and R$_b$, which are identical or different, represent a hydrogen atom or a linear or branched alkyl radical having a number of carbon atoms ranging from 1 to 10, and n represents an integer ranging from 0 to 20, may also be suitable as heat stabilizer.

According to the invention, in addition to the compounds of general formula (IV), other compounds including several nitroxyl radicals, such as, for example, those represented by the general formula (V), may also be suitable as heat stabilizer:

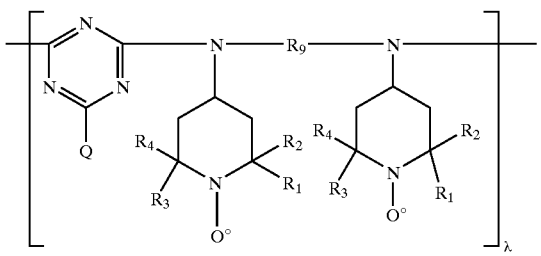

(V)

in which R$_1$, R$_2$, R$_3$ and R$_4$, which can be identical or different, have the same meaning as those of the preceding formulae (I) to (IV), G is an integer between 1 and 20, R$_9$ represents an alkylene group having a number of carbon atoms ranging from 2 to 12 which can be interrupted by an —O— or —NR$_{10}$— with R$_{10}$ denoting a hydrogen atom, an alkyl group having a number of carbon atoms of between 1 and 12, or a cycloalkyl group, and Q represents an —OR$_{11}$, —NHR$_{12}$ or —NR$_{12}$R$_{13}$ radical where R$_{11}$ represents a linear or branched alkyl radical having a number of carbon atoms ranging from 1 to 12, a C$_3$–C$_{12}$ alkoxyalkyl radical, a cyclohexyl radical, a benzyl radical, a phenyl radical, a tolyl radical or a 2,2,6,6-tetrapiperidinyl residue and R$_{12}$ and R$_{13}$ have the same meaning as R$_{11}$ and, furthermore, can also form, together and with the nitrogen atom which carries them, a 5-, 6- or 7-membered heterocyclic radical which can additionally comprise an oxygen.

The compounds of general formula (V) generally used are those obtained by oxidation of amines sold by Ciba under the name CHIMASORB 944, where R$_1$, R$_2$, R$_3$ and R$_4$ each denoting a methyl group, R$_9$ an alkylene group comprising 6 carbon atoms, Q representing an —N(O°)—C$_8$H$_{11}$ radical and λ being an integer between 2 and 4.

The preferred compounds of general formula (III) are those for which R$_1$, R$_2$, R$_3$ and R$_4$ each denote a methyl group, R$_5$, R$_6$, R$_7$ and R$_8$ each represent a hydrogen atom and X a —CHZ- group.

In particular, mention may be made, as compounds of general formula (III), of 2,2,6,6-tetramethyl-1-piperidinyloxy, generally sold under the name TEMPO, 4-hydroxy-2,2,6,6-tetramethyl-1-piperidinyloxy, sold under the name 4-hydroxy-TEMPO, 4-methoxy-2,2,6,6-tetramethyl-1-piperidinyloxy, commonly referred to as 4-methoxy-TEMPO, or 4-oxo-2,2,6,6-tetramethyl-1-piperidinyloxy, generally referred to as 4-oxo-TEMPO.

The compounds of general formula (III) which are particularly preferred are those represented by the following formula:

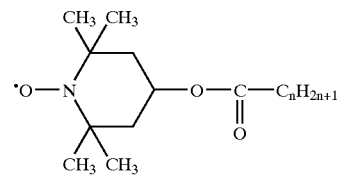

with n being able to vary from 1 to 20.

The compounds such as 2,2,5,5-tetramethyl-1-pyrrolidinyloxy, sold under the trade name PROXYL, 1-piperidinyloxy-2,2,6,6-tetramethyl-4-[(1-oxoocta-decyl)oxy], 1-piperidinyloxy-4,4'-((1,10-decanediyl)-bis(oxy)bis(2,2,6,6-tetramethyl) nitroxide, sold under the trade name CXA 5415 by Ciba Specialty Chemical, 2,2,6,6-tetramethyl-4-hydroxypiperidine-1-oxyl monophosphonate or 3-carboxy-2,2,5,5-tetramethylpyrrolidinyloxy (commonly referred to a 3-carboxy-Proxyl) are also preferred.

Noncyclic compounds, such as those represented by the general formula (VI), may also be suitable as heat stabilizers:

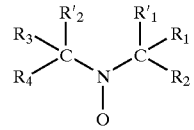

in which R$_1$, R$_2$, R$_3$, R$_4$, R'$_1$ and R'$_2$, which can be identical or different, have the same meaning as R$_1$, R$_2$, R$_3$ and R$_4$ of the preceding general formulae.

A second subject-matter of the invention is a composition comprising organic peroxide which is stable on storage and stable toward heat, characterized in that it comprises at least one organic peroxide and at least one heat stabilizer according to the first subject-matter of the present invention.

The amount of heat stabilizer present in the stable organic peroxide composition according to the invention is preferably between 0.1 and 99% by weight and advantageously between 0.2 and 30%.

Mention may in particular be made, as organic peroxides, of dialkyl peroxides, hydroperoxides and their salts, peroxyketals and peroxyesters. Dialkyl peroxides, in particular cyclic dialkyl peroxides deriving from the oxidation of ketones, peroxyketals and hydroperoxides are particularly preferred.

Mention may be made, as examples of dialkyl peroxides, of 2,5-dimethyl-2,5-di(tert-butylperoxy)hex-3-yne, di(tert-butyl) peroxide, di(tert-amyl) peroxide, tert-butyl cumyl peroxide, di(tert-butylperoxyisopropyl)benzene, 2,5-dimethyl-2,5-di(tert-butylperoxy)hexane, dicumyl peroxide or 3,6,9-triethyl-3,6,9-trimethyl-1,4,7-triperoxonane.

Mention may be made, as examples of peroxyesters, of tert-butyl peroxybenzoate, tert-butyl peroxyacetate, tert-butyl peroxy-3,5,5-trimethylhexanoate, 2,5-dimethyl-2,5-di(benzoylperoxy)hexane, OO-tert-butyl O-(2-ethylhexyl) monoperoxycarbonate, OO-tert-butyl O-isopropyl monoperoxycarbonate, OO-tert-amyl O-(2-ethylhexyl) monoperoxycarbonate, tert-butyl peroxyisobutyrate, tert-butyl peroxy-2-ethylhexanoate, tert-butyl peroxy-2-ethylhexanoate, tert-amyl peroxy-2-ethylhexanoate sold under the trade name (Luperox 575), 2,5-dimethyl-2,5-di(2-ethylhexanoylperoxy)hexane (Luperox® 256), 3,6,9-triethyl-1,4,7-triperoxonane, tert-butyl peroxypivalate (Luperox®

11M75), tert-amyl peroxypivalate, tert-butyl peroxyneodecanoate, tert-amyl peroxyneodecanoate, □-cumyl peroxyneodecanoate or 3-hydroxy-1,1-dimethylbutyl peroxyneodecanoate.

Mention may be made, as hydroperoxides, of tert-butyl hydroperoxide, tert-amyl hydroperoxide, cumyl hydroperoxide, 2,5-dimethyl-2,5-di(hydroxyperoxy)hexane, diisopropylbenzene monohydroperoxide, diisopropylbenzene dihydroperoxide or para-menthyl hydroperoxide.

Mention may be made, as hydroperoxide salts, of the disodium salt of 1,3- and 1,4-bis(2-hydroperoxideprop-2-yl)benzene.

Mention may be made, as peroxyketals, of ethyl 3,3-di(tert-butylperoxy)butyrate, ethyl 3,3-di(tert-amylperoxy)butyrate, n-butyl 4,4-di(tert-butylperoxy)valerate, 2,2-di(tert-butylperoxy)butane, 1,1-di(tert-butylperoxy)cyclohexane, 1,1-di(tert-butylperoxy)-3,5,5-trimethylcyclohexane or 1,1-di(tert-amylperoxy)cyclohexane.

Peroxyesters, such as Luperox® 575 (tert-amyl peroxy-2-ethylhexanoate), Luperox® 256 (2,5-dimethyl-2,5-di(2-ethylhexanoylperoxy)hexane) and Luperox® 11M75 (tert-butyl peroxypivalate), requiring a storage temperature below ambient temperature are advantageously chosen.

The organic peroxide composition according to the second subject-matter of the invention can also comprise conventional diluents, such as plasticizers, liquid phlegmatizers, organic solvents, polymeric carriers or organic carriers. This organic peroxide composition can additionally comprise one or more additives, such as anticaking agents, antioxidants, pigments or dyes, and metal-sequestering agents, such as DTPA (sodium diethylenetriaminepentaacetate) or EDTA (sodium ethylenediaminetetraacetate).

Mention may be made, as example of composition according to the second subject-matter of the invention, of the composition comprising the disodium salt of 1,3- and 1,4-bis(2-hydroxyperoxideprop-2-yl)benzene, a stabilizer according to the first subject-matter, in particular TEMPO, and a metal-sequestering agent, such as EDTA.

A third subject-matter of the invention is a process for the preparation of the organic peroxide composition according to the second subject-matter of the invention. This process consists in adding a sufficient amount of the heat stabilizer(s) according to the first subject-matter of the invention to the organic peroxide to be stabilized.

A fourth subject-matter of the invention is the use of the composition according to the second subject-matter of the invention for modifying polymers. Mention may in particular be made of the decomposition of polymers, in particular of polypropyene, and the grafting of polymers, such as, for example, the grafting of polypropylene with maleic anhydride.

EXAMPLES

Luperox® 101=2,5-dimethyl-2,5-di(tert-butylperoxy)hexane
Luperox® 802=1,4-bis(tert-butylperoxyisopropyl)benzene
Luperox® 331M50=1,1-di(tert-butylperoxy)

Luperox® TBH70X*=tert-butyl hydroperoxide
TEMPO: 2,2,6,6-tetramethyl-1-piperidinyloxy
AF845: 1-piperidinyloxy-2,2,6,6-tetramethyl-4-[(1-oxooctadecyl)oxy]
CXA 5415: 1-piperidinyloxy-4,4'-((1,10-decanediyl)bis(oxy)bis(2,2,6,6-tetramethyl) nitroxide
14% solution in isododecane The beneficial effect of the stabilizers (TEMPO, AF845 and CXA 5415) on the decomposition temperature of the various organic peroxides is illustrated in table I.

TABLE I

| Organic peroxide or mixture | Peroxide/ stabilizer ratio by mass | Temperature of the beginning of decomposition (° C.) |
| --- | --- | --- |
| Luperox 101 | — | 120 |
| Luperox ® 101 + TEMPO | 10 | 125 |
| Luperox ® 101 + AF 845 | 3 | 130 |
| Luperox ® 802 | — | 120 |
| Luperox ® 802 + TEMPO | 12 | 130 |
| Luperox ® 802 + AF 845 | 4 | 130 |
| Luperox ® 802 + CXA 5415 | 4 | 130 |
| Luperox ® 331M50 | — | 100 |
| Luperox ® 331M50 + TEMPO | 5 | 115 |
| Luperox ® TBH70X | — | 190 |
| Luperox ® TBH70X + TEMPO | 5 | 205 |

Products Used for the Decomposition
 Polypropylene with an MFI of 3.3 (230° C./2.16 kg)
 Organic peroxide: 2,5-dimethyl-2,5-di(tert-butylperoxy)hexane—Luperox® 101 (peroxide content 95%)
 Stabilizer: TEMPO Experimental Procedure The polypropylene is decomposed in a corotating twin-screw extruder of Brabender type. This extruder comprises 4 zones Z1 to Z4, the respective temperatures of which are 200° C./220° C./220° C./180° C. The extrusion rate at the outlet of zone Z4 depends on the screw speed; it typically varies from 4.5 to 5 kg/h. The lace is granulated after cooling. The product is characterized by the MFI value (measured at 230° C., 2.16 kg), by the value of the modulus (measured according to ISO Standard 178) and by the value of the Charpy impact test (measured at 23° C. according to ISO Standard 179/leA).

The polypropylene is reduced to the form of a powder, on which a solution based on acetone, on organic peroxide and on TEMPO is adsorbed. After adsorption, the acetone is evaporated and the polypropylene-based reactive mixture is introduced via a hopper into zone 1 (Z1).

The results obtained with regard to decomposition of the problem with a stabilizing composition according to the invention are summarized in table II (examples 3 and 4 carried out from organic peroxide and TEMPO compositions, whereas example 5 was carried out by dispersing the peroxide and the TEMPO separately over the polypropylene powder).

TABLE II

| Example | Peroxide (ppm) | TEMPO (ppm) | TEMPO/Peroxide molar ratio | MFI (dg/min) | Modulus (MPa) | Notched Charpy impact Energy at 23° C. (kJ/m$^2$) |
| --- | --- | --- | --- | --- | --- | --- |
| 1 | 0 | 0 | — | 3.3 | 1270 | 3.1 |
| 2 | 500 | 0 | 0.0 | 33.4 | 1170 | 2.3 |

TABLE II-continued

| Example | Peroxide (ppm) | TEMPO (ppm) | TEMPO/Peroxide molar ratio | MFI (dg/min) | Modulus (MPa) | Notched Charpy impact Energy at 23° C. (kJ/m$^2$) |
|---|---|---|---|---|---|---|
| 3 | 500* | 25* | 0.1 | 25.8 | 1170 | 2.6 |
| 4 | 2000* | 1020* | 1.0 | 23.6 | 1180 | 2.7 |
| 5 | 2000* | 1020 | 1.0 | 23.5 | 1180 | 2.7 |

*Use of a composition (premix) based on organic peroxide and on TEMPO

The incorporation of a composition based on organic peroxide and on nitroxide, such as TEMPO, makes it possible to obtain a polypropylene with a lower flow index and with a better impact property while retaining the same stiffness. Comparison of examples 4 and 5 clearly shows that the use of a premix results in properties identical to those obtained from the constituents used separately.

What is claimed is:

1. A process for preparing a thermally stable organic peroxide solution comprising admixing an organic peroxide and an N-heterocyclic heat-stabilizing compound comprising at least one nitroxyl radical with the N atom of the nitroxyl radical forming part of the ring, wherein the temperature of the beginning of decomposition of said solution comprising the stabilizer is greater than the temperature of the beginning of decomposition of the solution not comprising the stabilizer.

2. The process as claimed in claim 1, characterized in that the heat-stabilizing compound is represented by at least one of the following formulae (I), (II) and (III):

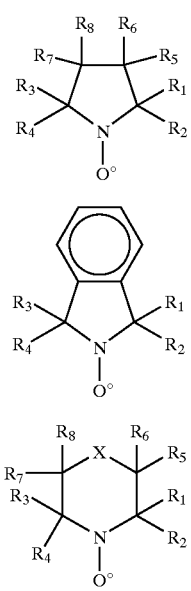

in which $R_1$, $R_2$, $R_3$ and $R_4$, which can be identical or different, represent a hydrogen atom, a halogen atom, a saturated or unsaturated and linear, branched or cyclic hydrocarbonaceous group a polymer chain or a functional group;

in which $R_5$, $R_6$, $R_7$ and $R_8$, which can be identical or different, can be chosen from the same family of group as that for $R_1$, $R_2$, $R_3$ and $R_4$ and, furthermore, can represent a hydroxyl group —OH or an acid group, such as —COOH or —PO(OH)$_2$ or —SO$_3$H;

X in the formula (III) representing:

a divalent group chosen from methylene —CH$_2$—, —C(OR°)(OR')—, carbonyl —C(O)—, oxy —O— and —CHZ-, with Z representing a monovalent residue chosen from cyano (—CN), hydroxyl (—OH), amino (—NR°R'), alkoxy (—OR°—), iminoyl (—N=CR°R'), carboxylate (—OC(O)—R°) or amide (—NHR°—C(O)R') groups and with R° and R', which are identical or different, representing a hydrogen atom, a linear or branched alkyl group having a number of carbon atoms ranging from 1 to 20, or a benzyl or phenyl group, or a phosphonate group —OP(O)RR' with R' and R' having the same meaning as Z.

3. The process as claimed in claim 2 wherein said halogen atom is selected from the group consisting of fluorine, chlorine, bromine, iodine, and a mixture thereof.

4. The process as claimed in claim 2 wherein said saturated or unsaturated and linear, branched or cyclic hydrocarbonaceous group comprises an alkyl or phenyl radical.

5. The process as claimed in claim 2 wherein said functional group is selected from the group consisting of a cyano group —CN, an ester group —COOR, an amide group —CON(R)$_2$, an alkoxyl group —OR, and a phosphonate group —PO(OR)$_2$, with R representing a hydrocarbonaceous chain having from 1 to 9 carbon atoms.

6. The process as claimed in claim 1, characterized in that the heat stabilizer is represented by the following formula:

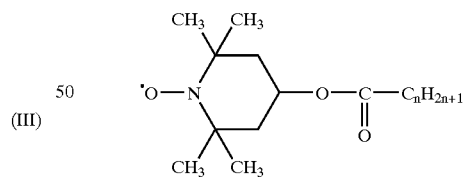

with n being able to vary from 1 to 20.

7. The process as claimed in claim 1, characterized in that the heat stabilizer is chosen from 2,2,6,6-tetramethyl-1-piperidinyloxy, 4-hydroxy-2,2,6,6-tetramethyl -1-piperidinyloxy, 4-methoxy-2,2,6,6-tetramethyl-1-piperidinyloxy, 4-oxo-2,2,6,6-tetramethyl-1-piperidinyloxy, 2,2,5,5,-tetramethyl-1-pyrrolidinyloxy, bis(1-oxyl-2,2,6,6-tetramethylpiperidin-4-yl) sebacate, 2,2,6,6-tetramethyl-4-hydroxypiperidine-1-oxyl monophosphonate or 3-carboxy-2,2,5,5-tetramethylpyrrolidinyloxy.

8. A composition comprising at least one organic peroxide which is/are stable on storage and stable toward heat, characterized in that it comprises at least one organic peroxide and at least one N-heterocyclic heat-stabilizing compound including at least one nitroxyl radical with the N atom of the nitroxyl radical forming part of the ring for preparing a thermally stable solution of organic peroxide, the temperature of the beginning of decomposition of said solution comprising the stabilizer being greater than the temperature of the beginning of decomposition of the solution not comprising the stabilizer.

9. The composition as claimed in claim 8, characterized in that the organic peroxide is selected from the group consisting of dialkyl peroxides, hydroperoxides and their salts, peroxyketals and peroxyesters.

10. The composition as claimed in claim 8, characterized in that the organic peroxide is dicumyl peroxide, 3,6,9-triethyl-3,6,9-trimethyl-1,4,7-triperoxonane or the disodium salt of 1,3- and 1,4-bis(2-hydroxyperoxideprop-2-yl)benzene.

11. A process for the manufacture of a composition as claimed in claim 8, characterized in that at least one N-heterocyclic heat-stabilizing compound including at least one nitroxyl radical with the N atom of the nitroxyl radical forming part of the ring for preparing a thermally stable solution of organic peroxide, the temperature of the beginning of decomposition of said solution comprising the stabilizer being greater than the temperature of the beginning of decomposition of the solution not comprising the stabilizer, is added to the organic peroxide.

* * * * *